(12) United States Patent
Vanderstraten et al.

(10) Patent No.: US 10,549,117 B2
(45) Date of Patent: Feb. 4, 2020

(54) GEOMETRIC ASPECTS OF RADIATION THERAPY PLANNING AND TREATMENT

(71) Applicant: Varian Medical Systems, Inc., Palo Alto, CA (US)

(72) Inventors: Reynald Vanderstraten, Brussels (BE); Eric Abel, San Jose, CA (US); Christel Smith, Santa Barbara, CA (US); Anthony Magliari, Swansea, IL (US); Timo Koponen, Espoo (FI); Josh Star-Lack, Palo Alto, CA (US)

(73) Assignees: Varian Medical Systems, Inc, Palo Alto, CA (US); Varian Medical Systems International AG., Cham (CH)

( * ) Notice: Subject to any disclaimer, the term of this patent is extended or adjusted under 35 U.S.C. 154(b) by 266 days.

(21) Appl. No.: 15/657,052

(22) Filed: Jul. 21, 2017

(65) Prior Publication Data

US 2019/0022409 A1 Jan. 24, 2019

(51) Int. Cl.
*A61N 5/10* (2006.01)

(52) U.S. Cl.
CPC .......... *A61N 5/103* (2013.01); *A61N 5/1081* (2013.01); *A61N 5/1043* (2013.01); *A61N 5/1045* (2013.01); *A61N 2005/1087* (2013.01)

(58) Field of Classification Search
CPC .......... A61N 5/1081; A61N 2005/1087; A61N 5/1045; A61N 5/103; A61N 5/1043; A61N 5/1031

See application file for complete search history.

(56) References Cited

U.S. PATENT DOCUMENTS

| | | | |
|---|---|---|---|
| 6,580,084 B1 | 6/2003 | Hiramoto et al. |
| 6,888,832 B2 | 5/2005 | Richardson et al. |
| 7,423,278 B2 | 9/2008 | Amaldi et al. |
| 7,554,275 B2 | 6/2009 | Amaldi |
| 7,778,691 B2 | 8/2010 | Zhang et al. |
| 8,071,966 B2 | 12/2011 | Kaiser et al. |

(Continued)

FOREIGN PATENT DOCUMENTS

| | | |
|---|---|---|
| EP | 3043863 A1 | 7/2016 |
| EP | 3103519 | 12/2016 |

(Continued)

OTHER PUBLICATIONS

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

(Continued)

*Primary Examiner* — Christine H Matthews
*Assistant Examiner* — Joshua Daryl D Lannu

(57) ABSTRACT

Radiation treatment planning includes determining a number of beams to be directed into a target, determining directions (e.g., gantry angles) for the beams, and determining an energy level for each of the beams. The number of beams, the directions of the beams, and the energy levels are determined such that the beams do not overlap outside the target and the prescribed dose will be delivered across the entire target.

16 Claims, 12 Drawing Sheets

(56) References Cited

U.S. PATENT DOCUMENTS

| | | |
|---|---|---|
| 8,121,253 B2 | 2/2012 | Nelms |
| 8,253,121 B2 | 8/2012 | Gnutzmann et al. |
| 8,405,056 B2 | 3/2013 | Amaldi et al. |
| 8,406,844 B2 | 3/2013 | Ruchala et al. |
| 8,618,521 B2 | 12/2013 | Loo et al. |
| 8,636,636 B2 | 1/2014 | Shukla et al. |
| 8,644,571 B1 * | 2/2014 | Schulte ............. A61N 5/1039 250/307 |
| 8,699,664 B2 | 4/2014 | Otto et al. |
| 8,798,343 B2 | 8/2014 | Kabus et al. |
| 8,901,519 B2 | 12/2014 | Schardt et al. |
| 8,986,186 B2 | 3/2015 | Zhang et al. |
| 9,018,603 B2 | 4/2015 | Loo et al. |
| 9,033,859 B2 | 5/2015 | Fieres et al. |
| 9,149,656 B2 | 10/2015 | Tanabe |
| 9,636,525 B1 | 5/2017 | Sahadevan |
| 2006/0274061 A1 | 12/2006 | Wang et al. |
| 2007/0034812 A1 | 2/2007 | Ma et al. |
| 2008/0049897 A1 | 2/2008 | Molloy |
| 2008/0226030 A1 * | 9/2008 | Otto ............. A61N 5/1031 378/65 |
| 2011/0006214 A1 | 1/2011 | Boenig |
| 2012/0136194 A1 | 5/2012 | Zhang et al. |
| 2015/0011817 A1 | 1/2015 | Feng |
| 2015/0057484 A1 | 2/2015 | Amaldi |
| 2015/0306423 A1 | 10/2015 | Bharat et al. |
| 2016/0193482 A1 | 7/2016 | Fahrig et al. |
| 2017/0028220 A1 | 2/2017 | Schulte et al. |

FOREIGN PATENT DOCUMENTS

| | | |
|---|---|---|
| JP | 2014161706 A | 9/2014 |
| JP | 2017098000 A | 6/2017 |

OTHER PUBLICATIONS

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-647 https://accelconf.web.cern.ch/accelconf/p01/PAPERS/FOAA004.PDF.

Th. Haberer,W. Becher,D. Schardt,G. Kraft "Magnetic scanning system for heavy ion therapy" Nuclear Instruments and Methods in Physics Research Section A: Accelerators, Spectrometers, Detectors and Associated Equipment , NIM, Elsevie, Jun. 10 1993, vol. 330, Issues 1-2, Jun. 10, 1993, pp. 296-305.

Amaldi, TERA Foundation, Novara, Italy A. Degiovanni, CERN, Geneva, Switzerland Linac 2014. Proton and Carbon Linacs for Hadron Therapy U. http://accelconf.web.cern.ch/AccelConf/LINAC2014/papers/friob02.pdf. pp. 1207-1212.

Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.

Favaudon V, Caplier L, Monceau V, Pouzoulet F, Sayarath M, Fouillade C, Poupon MF, Brito I, Hupé P, Bourhis J, Hall J, Fontaine JJ, Vozenin MC. Ultrahigh dose-rate Flash irradiation increases the differential response between normal and tumor tissue in mice. Sci Transl Med. Jul. 16, 2014;6(245):245ra93. doi: 10.1126/scitranslmed.3008973. PubMed PMID: 25031268.

Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.

M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.

K. Peach, et al. "PAMELA—A Model for an FFAG Based Hadron Therapy Machine", Proceedings of PAC07, Albuquerque, New Mexico, USA. pp. 2880-2882.

S. Benedetti, A. Grudiev, and A. Latina Phys. Rev. Accel. Beams 20, 040101—Published Apr. 13, 2017.

Z. Li, et. al., Normal conducting cw transverse crab cavity for producing short pulses in spear3, Proceedings of IPAC2017, Copenhagen, Denmark. pp. 2840-2843.

Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010. American Institute of Physics.

Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].

S. Tantawi, Z. Li , et al. patent pending, Title: "Distributed Coupling and Multi-Frequency Microwave Accelerators", Filed: Jul. 9, 2014, U.S. Appl. No. 62/022,469.

S.Tantawi , M.Nasr, "Designs and High Power Tests of Distributed Coupling Linacs " IFIC, Jun. 13-16, 2017 , Valencia , Spainhttps://indico.cem.ch/event/589548/contributions/2615455/attachments/1479738/2294080/Mamdouh_High_Gradient_2017.pdf.

Jensen, Aaron, Jeff Neilson, and Sami Tantawi. "X-band multi-beam klystron design and progress report." Vacuum Electronics Conference (IVEC), 2015 IEEE International. IEEE, 2015.

K.Halbach, "Design of permanent multipole magnets with oriented rare earth cobalt material" , Nuclear Instruments and Methods , vol. 169, Issue 1, Feb. 1, 1980, pp. 1-12 [http://www.sciencedirect.com/science/article/pii/0029554X80900944].

J. K. Lim, P. Frigola, G. Travish, J. B. Rosenzweig, S. G. Anderson, W. J. Brown, J. S. Jacob, C. L. Robbins, and A. M. Tremaine, "An Adjustable, short focal length permanent-magnet quadrupole based electron beam final focus system" Phys. Rev. ST Accel. Beams 8, 072401—Published Jul. 15, 2005. 19 pages.

Sayyed Bijan Jiaa, Mohammad Hadi Hadizadeha, Ali Asghar Mowlavi ,Mandy Ebrahimi Loushab "Evaluation of energy deposition and secondary particle production in proton therapy of brain using a slab head phantom" Elsevier , Reports of Practical Oncology & Radiotherapy,vol. 19, Issue 6, Nov.-Dec. 2014, pp. 376-384.

J.Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.

Lisa Polster, Jan Schuemann, Ilaria Rinaldi, Lucas Burigo, Aimee Louise McNamara, Robert D Stewart, Andrea Attili, David J. Carlson, Alejandro Carabe-Fernadez, Bruce Faddegon, Joseph Perl, and Harald Paganetti, "Extension of TOPAS for the simulation of proton radiation on molecular and cellular endpoints," Phys Med Biol. Jun. 10, 2015;60(13):5053-5070, PMID: 26061583.

Vladimir A. Bashkirov a,n , Robert P. Johnson b , Hartmut F.-W. Sadrozinski b , Reinhard W. Schulte a "Development of proton computed tomography detectors for applications in hadron therapy" , NIM Nuclear Instruments and Methods in Physics Research A ( under press a the time of writing proposal) http://www.sciencedirect.com/science/article/pii/S0168900215009274.

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39(11)/7140/13, 13 pages.

Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis,Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages.

(56) References Cited

OTHER PUBLICATIONS

Valerie Devillaine, Radiotherapy and radiation biology, Radiotherapy—new treatment methods, Radio-toxicity, radio resistance and pediatric cancers, Photo-sensitization and retinoblastoma, 6 pages.
Radiotherapy "flashes" to reduce side effects, An effect for each mode of administration, Images of tissue sections, Ultra-high dose-rate, Science Translational Medicine, Jul. 16, 2014, 3 pages.
To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.

* cited by examiner

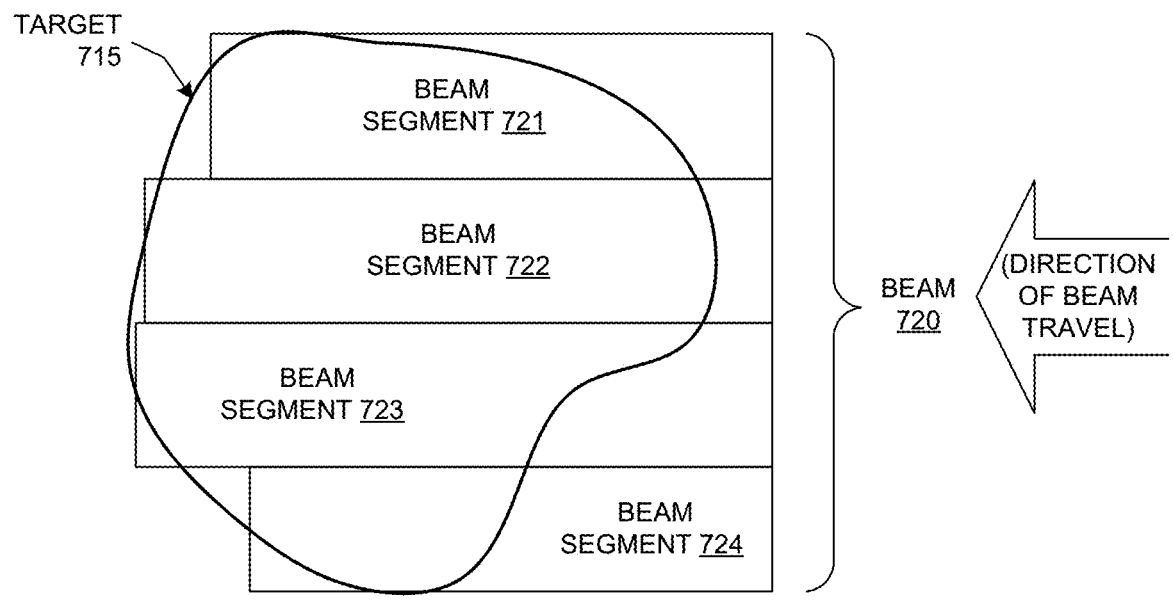

GEOMETRIC ASPECTS OF RADIATION THERAPY PLANNING AND TREATMENT

RELATED U.S. APPLICATION

This application is related to U.S. application Ser. No. 15/657,094, now U.S. Pat. No. 10,092,774, by R. Vanderstraeten et al., entitled "Dose Aspects of Radiation Therapy Planning and Treatment," filed Jul. 21, 2017, and hereby incorporated by reference in its entirety.

BACKGROUND

The use of radiation therapy to treat cancer is well known. Typically, radiation therapy involves directing a beam of high energy proton, photon, ion, or electron radiation ("therapeutic radiation") into a target or target volume (e.g., a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the target while minimizing exposure of surrounding normal, healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. FLASH RT thus introduces important constraints that are not considered in or achieved with conventional radiation treatment planning.

SUMMARY

In intensity modulated radiation therapy (IMRT) such as intensity modulated particle therapy (IMPT), beam intensity is varied across each treatment region (target) in a patient. Depending on the treatment modality, the degrees of freedom available for intensity modulation include beam shaping (collimation), beam weighting (spot scanning), and angle of incidence (which may be referred to as beam geometry). These degrees of freedom lead to effectively an infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Embodiments according to the present invention provide an improved method of radiation treatment planning, and improved radiation treatment based on such planning, for FLASH radiation therapy (FLASH RT). In embodiments, a prescribed dose to be delivered into and uniformly across the target is determined. Directions (e.g., gantry angles relative to the patient or target, or nozzle directions relative to the patient or target) for delivering beams into the target are determined. This can include determining the number of beams (the number of directions from which beams are to be delivered). The directions are determined such that the beams do not overlap outside the target; that is, to take advantage of the normal tissue sparing effect of FLASH RT, each sub-volume of normal (healthy) tissue is irradiated only once. The beams can overlap inside the target. The beams' paths can lie within the same plane, or they can be in different planes. An energy for each of the beams is also determined. The number of beams, the directions of the beams, and beam energies are determined such that the calculated or predicted cumulative doses inside the target satisfy the prescribed dose across the target. An iterative process can be used to determine the number of beams, the directions of the beams, and beam energies.

In embodiments, a beam energy is determined for each of the directions (for each of the beams). The beam energy for each direction is determined such that calculated cumulative doses across the target (at locations inside the target where the beams' paths overlap) satisfy the prescribed dose. In embodiments, a beam includes a number of beam segments or beamlets. In one or more such embodiments, a maximum energy for the beam is specified, and an energy for each of the beam segments is determined as a percentage (100 percent or less) or equivalent fraction of the maximum beam energy. In general, beams can have the same energy or different energies, and each beam can have a range of energies. Thus, different energies can be delivered in different directions, and different energies can be delivered in each direction.

Embodiments according to the invention improve radiation treatment planning and the treatment itself by expanding FLASH RT to a wider variety of treatment platforms and target sites (e.g., tumors). Treatment plans generated as described herein are superior for sparing normal tissue from radiation in comparison to conventional techniques for FLASH dose rates and even non-FLASH dose rates by reducing, if not minimizing, the magnitude of the dose, and in some cases the integrated dose, to normal tissue (outside the target) by design. When used with FLASH dose rates, management of patient motion is simplified. Treatment planning, while still a complex task, is simplified relative to conventional planning.

In summary, embodiments according to this disclosure pertain to generating and implementing a treatment plan that is the most effective (relative to other plans) and with the least (or most acceptable) side effects (e.g., the lowest dose outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computer systems because, for example, by reducing the complexity of generating treatment plans, fewer computational resources are needed and consumed to develop the plans, meaning also that computer resources are freed up to perform other tasks.

In addition to IMRT and IMPT, embodiments according to the invention can be used in spatially fractionated radiation therapy including high-dose spatially fractionated grid radiation therapy and microbeam radiation therapy.

These and other objects and advantages of embodiments according to the present invention will be recognized by one skilled in the art after having read the following detailed description, which are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

FIG. 7C illustrates a cross-sectional view of a target and a beam including beam segments in embodiments according to the invention.

FIG. 8 is a flowchart of an example of a computer-implemented radiation treatment method in embodiments according to the present invention.

DETAILED DESCRIPTION

Figure 1:
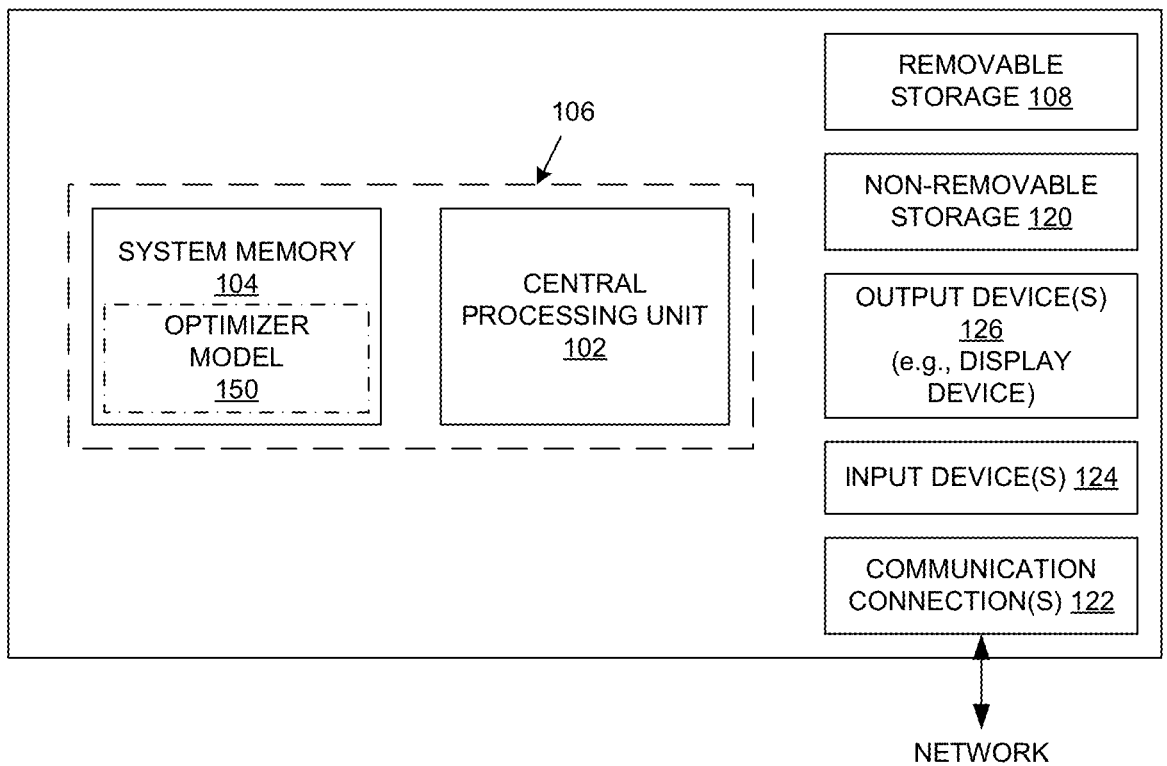
FIG. 1 is a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," or the like, refer to actions and processes (e.g., the flowcharts of FIGS. 5 and 8) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein (e.g., FIGS. 5 and 8) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
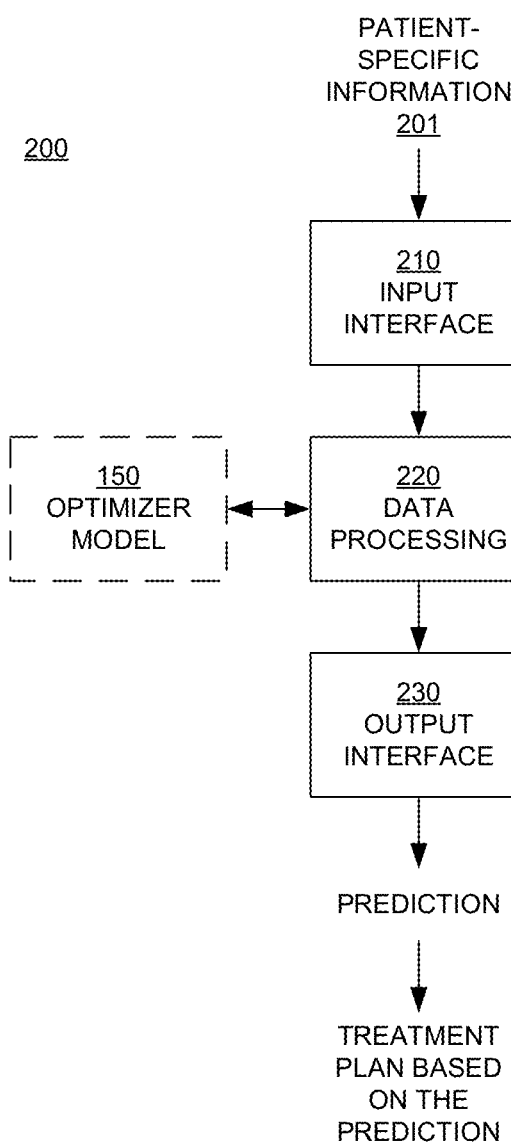
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
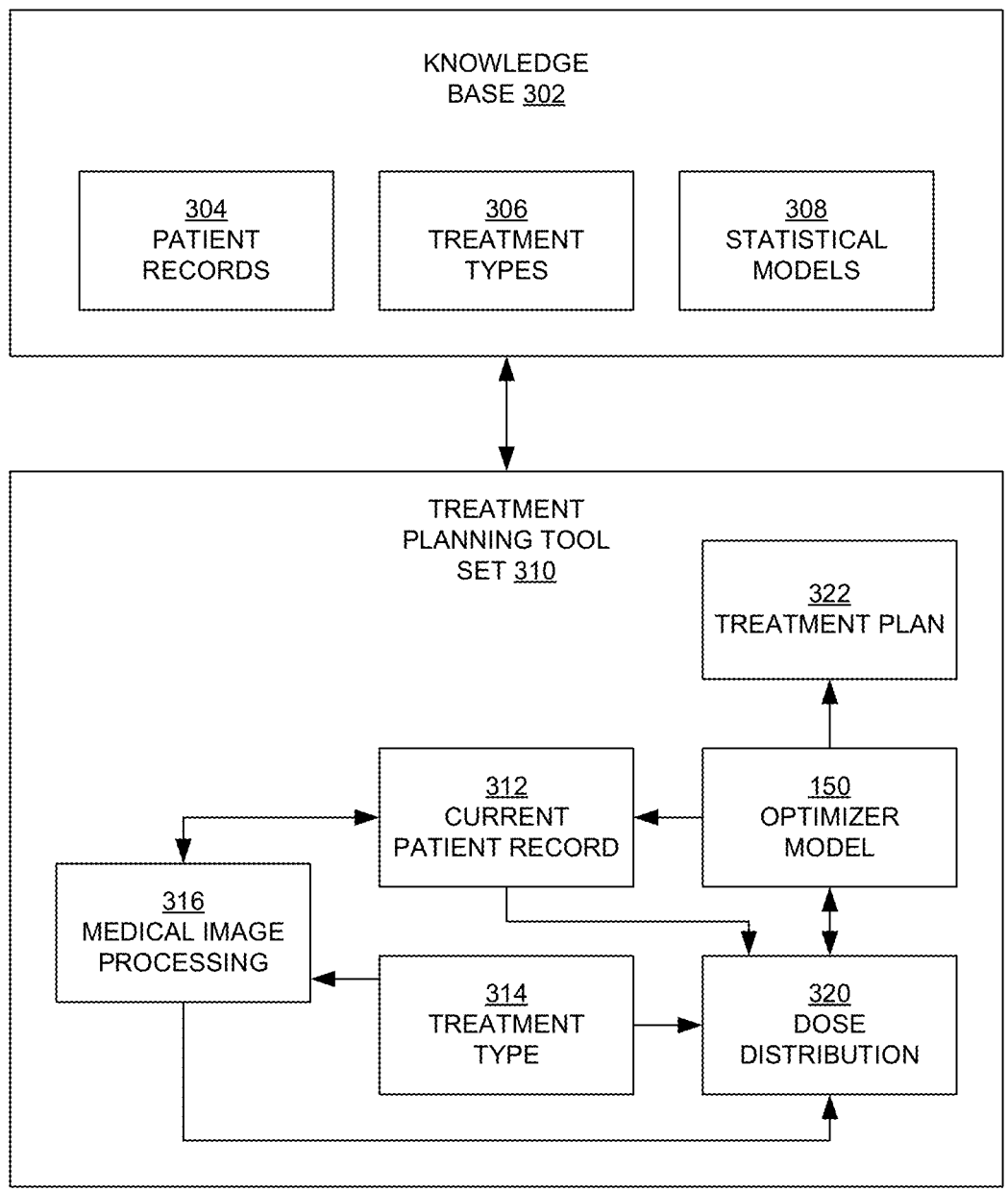
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography or magnetic resonance imaging) to form a three-dimensional (3D) image using the medical images in the current patient record 312. Dose distribution maps are calculated by the dose distribution module 320, which may utilize the optimizer model 150.

In embodiments according to the present invention, the optimizer model 150 uses a dose prediction model to help shape the dose distribution. The optimizer model 150 can provide, for example, a 3D dose distribution, fluences, and associated dose-volume histograms for the current patient.

Figure 4A:
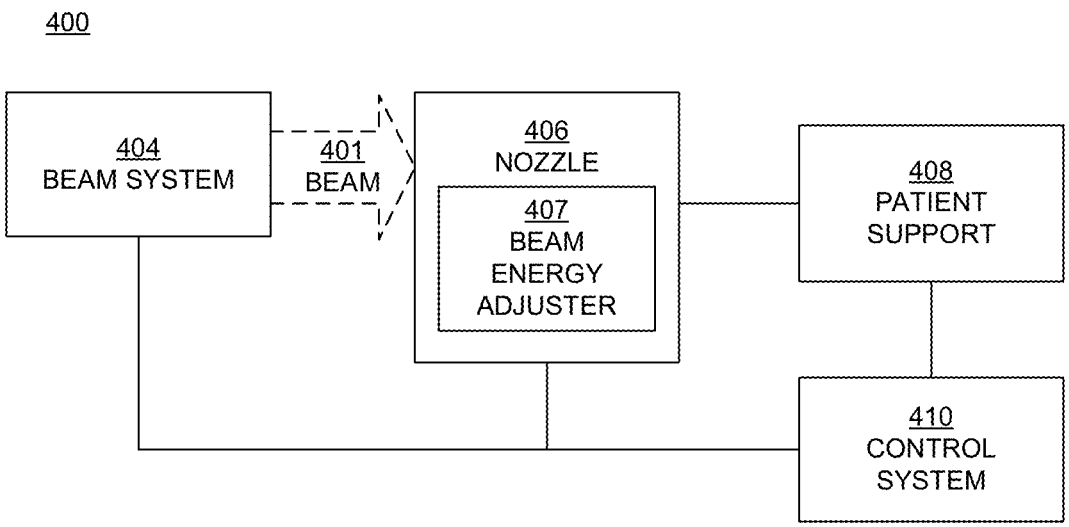
FIG. 4A is a block diagram showing selected components of a radiation therapy system upon which embodiments according to the present invention can be implemented.

FIG. 4A is a block diagram showing selected components of a radiation therapy system 400 upon which embodiments according to the present invention can be implemented. In the example of FIG. 4A, the system 400 includes a beam system 404 and a nozzle 406.

The beam system 404 generates and transports a beam 401 to the nozzle 406. In general, the beam 401 can be a proton beam, electron beam, photon beam, ion beam, or atom nuclei beam (e.g., carbon, helium, and lithium). In embodiments, the beam 401 is a proton beam. In another embodiment, the beam 401 is an ion beam.

In embodiments, depending on the type of beam, the beam system 404 includes components that direct (e.g., bend, steer, or guide) the beam through the system in a direction toward and into the nozzle 406. In embodiments, the radiation therapy system 400 may also include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 may be mounted on or a part of a gantry (FIGS. 4B, 4C, and 4D) that can be moved relative to the patient support device 408, which may also be moveable. In embodiments, the accelerator and beam transport system 404 is also mounted on or is a part of the gantry. In another embodiment, the accelerator and beam transport system is separate from (but in communication with) the gantry.

The nozzle 406 is used to aim the beam toward various locations (a target) within an object (e.g., a patient) supported on the patient support device 408 in a treatment room. In embodiments, the patient support device 408 is a table or couch that supports the patient in a supine position. In another embodiment, the patient support device 408 is a chair in which the patient sits. A chair can offer some advantages relative to a couch or table. Some patients are uncomfortable in a supine position or find it difficult to stay in that position. A chair can be moved more easily than a couch. A chair can have more degrees of freedom relative to a couch. In other words, by using a chair, it may be possible to more comfortably change the position of the patient relative to the nozzle 406 in more ways than are possible using a couch. As such, use of a chair to move the patient relative to the nozzle 406 may reduce the number of times the heavier gantry needs to be moved or eliminate the need to move the gantry at all. If the gantry does not need to be moved, then the nozzle 406 can remain stationary, pointing in a single direction with the beam directed only towards one wall of the treatment room. Consequently, thicker shielding would be needed only for that one wall, reducing costs and also reducing the overall room footprint. The magnitude of motion for an upright position in a chair is also smaller than lying down on a couch. This is favorable for high-precision treatments. In addition, absolute lung volumes are larger in the upright position, which can reduce mean lung dose. A chair also provides larger solid angle coverage, no collisions, and real time tracking.

A target may be an organ, a portion of an organ (e.g., a volume or region within the organ), a tumor, diseased tissue, or a patient outline.

The control system 410 of FIG. 4A receives and implements a prescribed treatment plan. In embodiments, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and/or shape of the beam, according to data it receives and according to the prescribed treatment plan.

As noted above, the beam entering the nozzle 406 has a specified energy. Thus, in embodiments according to the present disclosure, the nozzle 406 includes one or more components that affect (e.g., decrease, modulate) the energy of the beam. The term "beam energy adjuster" is used herein as a general term for a component or components that affect the energy of the particles in the beam, in order to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster can control the location of the Bragg peak in the target. In various embodiments, the beam energy adjuster 407 includes a range modulator, a range shifter, or both a range modulator and a range shifter. That is, when the term "beam energy adjuster" is used, then the element being discussed may be a range modulator, a range shifter, or both a range modulator and a range shifter. Examples of a beam energy adjuster for proton beams and ion beams are disclosed in the co-pending patent application, U.S. application Ser. No. 15/089,330, now U.S. Pat. No. 9,855,445, entitled "Radiation Therapy Systems and Methods for Delivering Doses to a Target Volume"; however, the invention is not so limited.

Figure 4B:
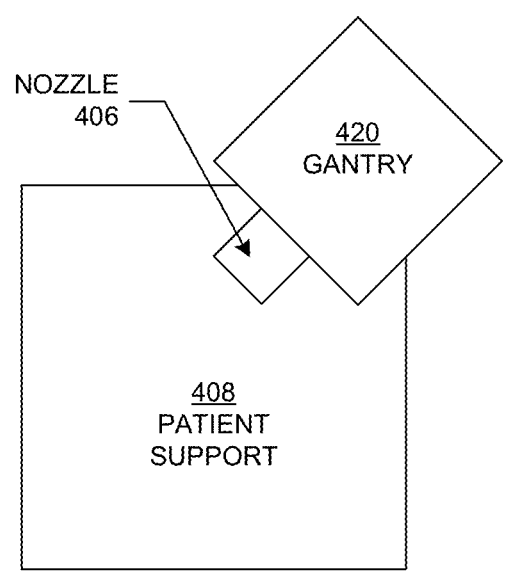
FIG. 4B is a block diagram illustrating a non-coplanar arrangement of a gantry and nozzle relative to a patient support device in embodiments according to the invention.
Figure 4C:
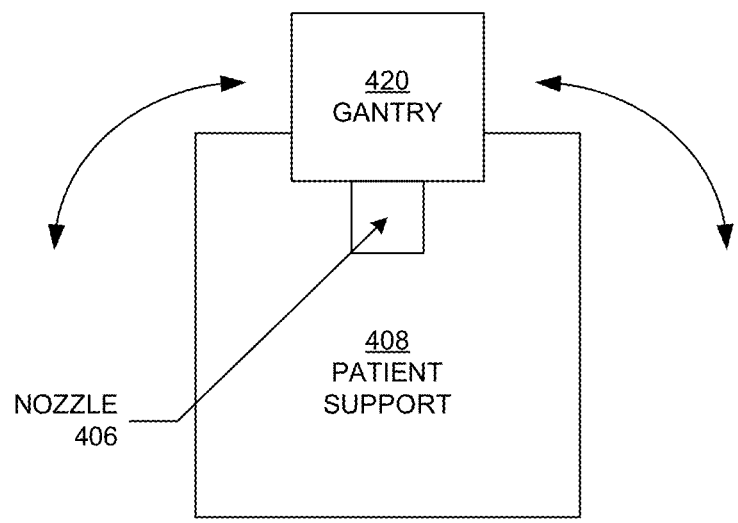
FIG. 4C is a block diagram illustrating a coplanar arrangement of a gantry and nozzle relative to a patient support device in embodiments according to the invention.
Figure 4D:
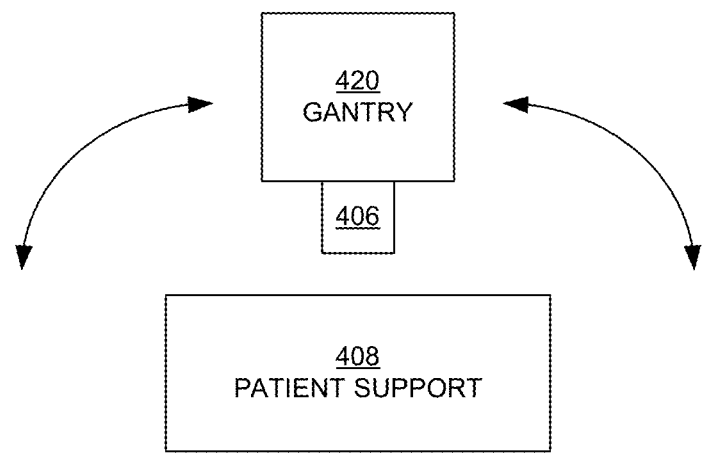
FIG. 4D is a block diagram illustrating movement of a gantry and nozzle around a patient support device in embodiments according to the invention.

FIG. 4B is a block diagram illustrating a non-coplanar arrangement of a gantry 420 and nozzle 406 relative to a patient support device 408 in embodiments according to the invention. FIG. 4C is a block diagram illustrating a coplanar arrangement of a gantry 420 and nozzle 406 relative to a patient support device 408 and also illustrating movement of the gantry and nozzle around the patient support device in embodiments according to the invention. FIG. 4D is a block diagram illustrating movement of the gantry 420 and nozzle 406 around the patient support device 408 in embodiments according to the invention. This movement can occur in either the non-coplanar arrangement or the coplanar arrangement.

Figure 5:
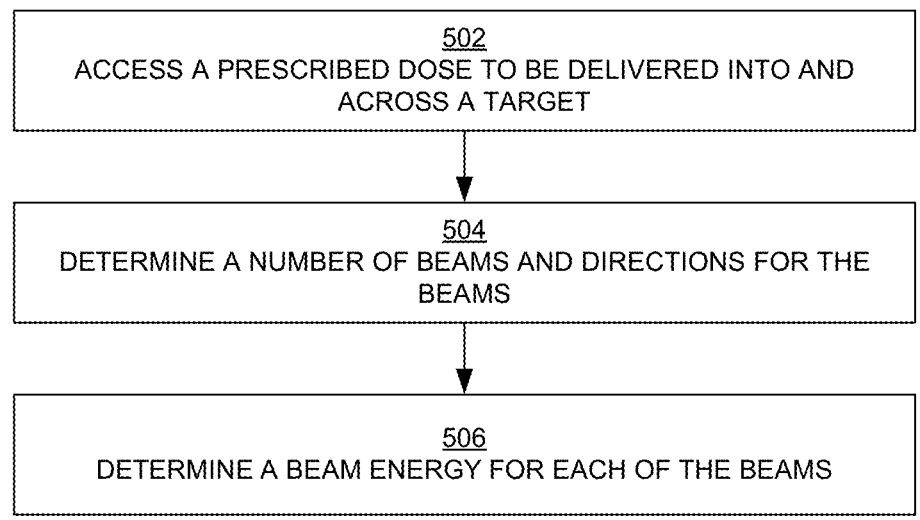
FIG. 5 is a flowchart of an example of computer-implemented operations for generating a radiation treatment plan in embodiments according to the present invention.

FIG. 5 is a flowchart 500 of an example of computer-implemented operations for generating a radiation treatment plan in embodiments according to the present invention. The flowchart 500 can be implemented as computer-executable instructions (e.g., the optimizer model 150 of FIG. 1) residing on some form of computer-readable storage medium (e.g., using the computing system 100 of FIG. 1).

In intensity modulated radiation therapy (IMRT) such as intensity modulated particle therapy (IMPT), beam intensity is varied across each treatment region (target) in a patient. Depending on the treatment modality, the degrees of freedom available for intensity modulation include beam shaping (collimation), beam weighting (spot scanning), and angle of incidence (which may be referred to as beam geometry). These degrees of freedom lead to effectively an infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

In block 502 of FIG. 5, a prescribed dose to be delivered into and across the target is determined or accessed from a memory of a computing system. Each portion of the target can be represented by at least one 3D element known as a voxel; a portion may include more than one voxel. A portion of a target or a voxel may also be referred to herein as a sub-volume; a sub-volume may include one or more portions or one or more voxels. As will be described in detail below, each portion or voxel may receive radiation from one or more beams delivered from different directions. The prescribed dose defines, for example, a dose value, or a minimum dose value and a maximum dose value, for each portion or voxel of the target. In embodiments, the prescribed dose is the same for all portions (sub-volumes or voxels) of the target, such that a uniform dose is prescribed for the entire target.

In block 504, directions (e.g., gantry angles relative to the patient or target, or nozzle directions relative to the patient or target) for delivering beams into the target are determined or accessed from a memory of a computing system. The operation of determining or accessing beam directions also includes determining or accessing the number of beams (the number of directions from which beams are to be delivered). In general, when generating the radiation treatment plan, one goal is to determine beam paths that minimize the irradiation time of each sub-volume or voxel of the tissue outside the target. Ideally, each sub-volume or voxel outside the target is intersected, at most, by only a single beam. That is, ideally, the beams' paths do not overlap outside the target. If some overlap between beam paths is permitted, then ideally each sub-volume or voxel outside the target is intersected by not more than two beams, with most intersected by only a single beam. In embodiments, as one means of achieving the aforementioned goal, the directions are determined such that the total amount of overlap between the beams' paths is minimized outside the target. In another such embodiment, the directions are determined so that the paths of the beams do not overlap at all outside the target. The beams' paths can overlap within the target. The beams' paths can lie within the same plane, or they can be in different planes. Additional information is provided in conjunction with FIGS. 6A, 6B, and 6C.

Any number of other factors may be considered when determining the beam directions. These factors may include the shape and size (e.g., height H and width W, or diameter) of the beam in the beam's eye view (see FIG. 7A). These factors may also include, for example, the amount or type of healthy tissue that a beam will be traveling through. That is, one beam direction may be more favorable than another if it travels a shorter distance through healthy tissue or avoids passing through a vital organ and may be weighted accordingly.

In block 506 of FIG. 5, a beam energy or intensity is determined for each of the directions (for each of the beams) or accessed from a memory of a computing system. The beam energy or intensity for each direction is determined such that the predicted or calculated cumulative doses (e.g., doses calculated using the optimizer model 150 of FIG. 1) at locations inside the target satisfy the prescribed dose as defined in block 502. The beam energy or intensity for each direction is determined such that the predicted or calculated cumulative doses (e.g., doses calculated using the optimizer model 150 of FIG. 1) inside the target satisfy the prescribed dose as defined in block 502. In embodiments, a beam includes a number of beam segments or beam lets. In one or more such embodiments, a maximum energy (e.g., 80 MeV) for the beam is specified, and an energy for each of the beam segments is determined as a percentage (100 percent or less) or equivalent fraction of the maximum beam energy. In general, beams can have the same energy or different energies, and each beam can have a range of energies. Thus, different energies or intensities can be delivered in different directions, and different energies or intensities can be delivered in each direction. Additional information is provided in conjunction with FIGS. 7A, 7B, and 7C.

While the operations in blocks 502, 504, and 506 of FIG. 5 are presented as occurring in series and in a certain order, the present invention is not so limited. The operations may be performed in a different order and/or in parallel, and they may also be performed in an iterative manner, as the number of beams (and accordingly, the number of directions), the beam directions, and the beam energies or intensities (and/or beam segment energies or intensities) used to deliver the prescribed dose are interrelated. The number of beams, their directions, and their energies are determined such the calculated or predicted dose at all the sub-volumes or voxels is the same or within a specified tolerance such that a uniform or satisfactorily uniform dose (the prescribed dose) is delivered across the entire target. In particular, in embodiments, the beams are not allowed to overlap outside the target; with this limitation, the number of beams, their directions, and their energies are determined such the prescribed dose is delivered across the entire target. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computing system 100 (FIG. 1) for radiation treatment planning as disclosed herein is important.

Once a final set of values for number of beams, their directions, and their energies are determined, then those values (as well as other values for other parameters known in the art) can be stored as a radiation treatment plan in the memory of a computer system, from which it can be subsequently accessed.

Figure 6A:
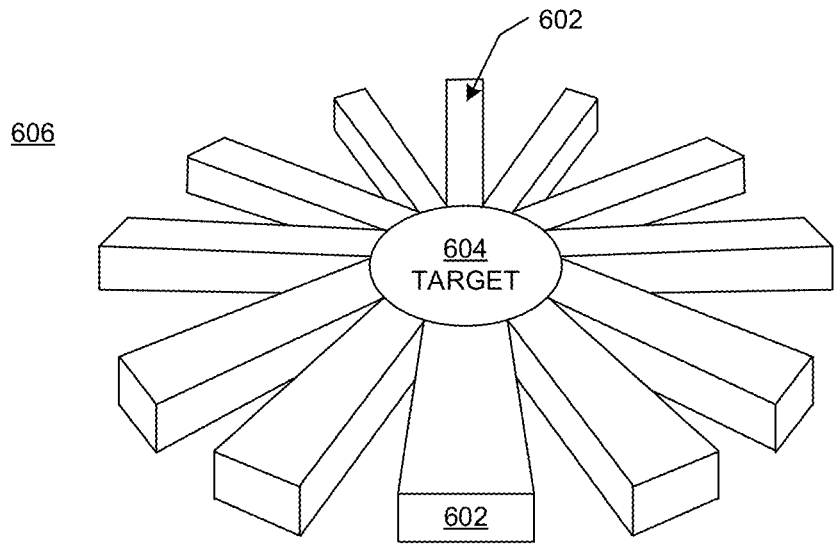
FIG. 6A illustrates a perspective view of an example of a beam geometry in embodiments according to the invention.

FIG. 6A illustrates a perspective view of an example of a beam geometry in embodiments according to the invention. In the example of FIG. 6A, the beams (exemplified by beam 602) are in the same plane. Each beam can deliver a relatively high dose in a relatively short period of time. For example, in embodiments, each beam can deliver doses sufficient for FLASH RT (e.g., at least four (4) grays (Gy) in less than one second, and as much as 20 Gy or 50 Gy or more in less than one second). In embodiments, the range is 0.01-500 Gy. As described herein, each beam can include one or more beam segments or beam lets. In this example, the beams' paths overlap only within the target 604, and do not overlap outside the target in the surrounding tissue 606.

Although multiple beams are shown in FIG. 6A, this does not mean that all beams are necessarily delivered at the same time or in overlapping time periods, although they can be. The number of beams delivered at any one time depends on the number of gantries or nozzles in the radiation treatment system (e.g., the radiation treatment system 400 of FIG. 4A) and on the treatment plan.

Figure 6B:
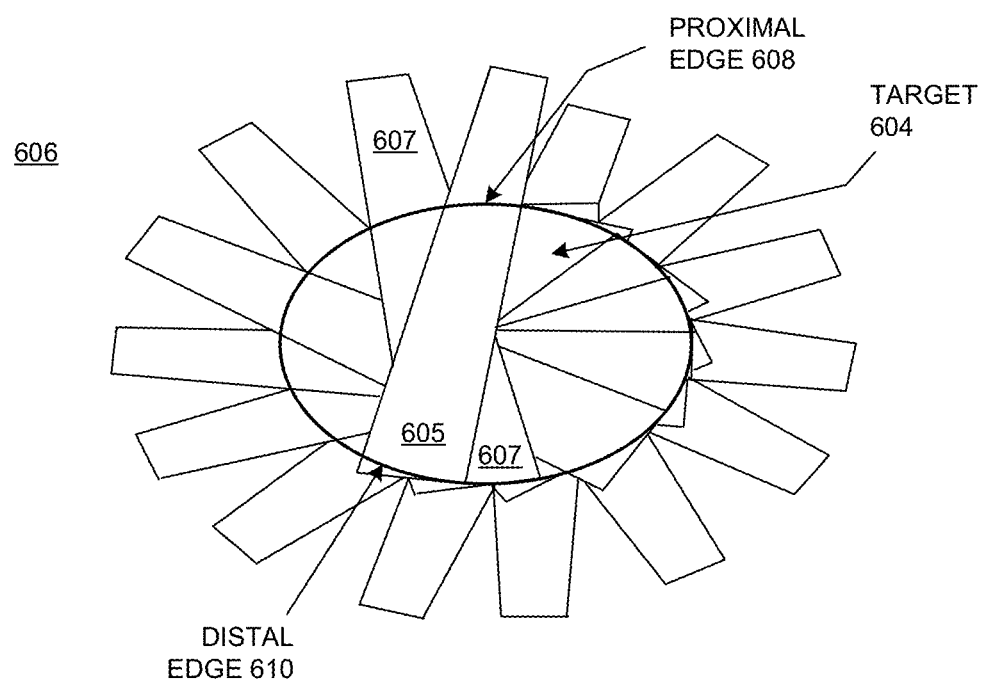
FIG. 6B illustrates a cross-sectional view of an example of a beam geometry in embodiments according to the invention.

FIG. 6B illustrates a cross-sectional view of an example of a beam geometry in embodiments according to the invention. In this example, the beams (exemplified by beams 605 and 607) overlap only within the target and are in the same plane. The figure depicts the beams in overlapping fashion to demonstrate that each portion of the target 604 receives a dose of radiation.

In the examples of FIGS. 6A and 6B, the beams are illustrated as not extending beyond the distal edge of the target 604 (as could be the case for a proton beam or an ion beam); however, the invention is not so limited. Each beam can deliver a relatively high dose in a relatively short period of time. For example, each beam can deliver doses sufficient for FLASH RT.

As will be discussed further in conjunction with FIG. 7C, for implementations in which the beams have a Bragg peak, such as a proton beam or an ion beam, the dose delivered by a beam (or beam segment) is not necessarily uniform along the entire length of the beam path through the target 604. Thus, for example, for a proton or ion beam, the dose delivered by the beam 605 at the proximal portion (or edge) 608 of the target 604 may be different from (e.g., less than) the dose delivered by that beam at the distal portion (or edge) 610 of the target (here, proximal and distal are with reference to the source of the beam 605). The same can be said for each proton or ion beam.

The dose delivered to each portion of the target 604 is cumulative, based on the number of beams that are delivered to and through that portion. For example, the portions of the target 604 covered by the beams 605 and 607 receive a total dose that is the sum of the dose delivered by the beam 605 and the dose delivered by the beam 607. In embodiments, the energies of the beams (beam segments) are accurately determined so that, even though the dose along each beam (or beam segment) is not uniform, a uniform cumulative dose distribution is achieved within and across the target 604.

Figure 6C:
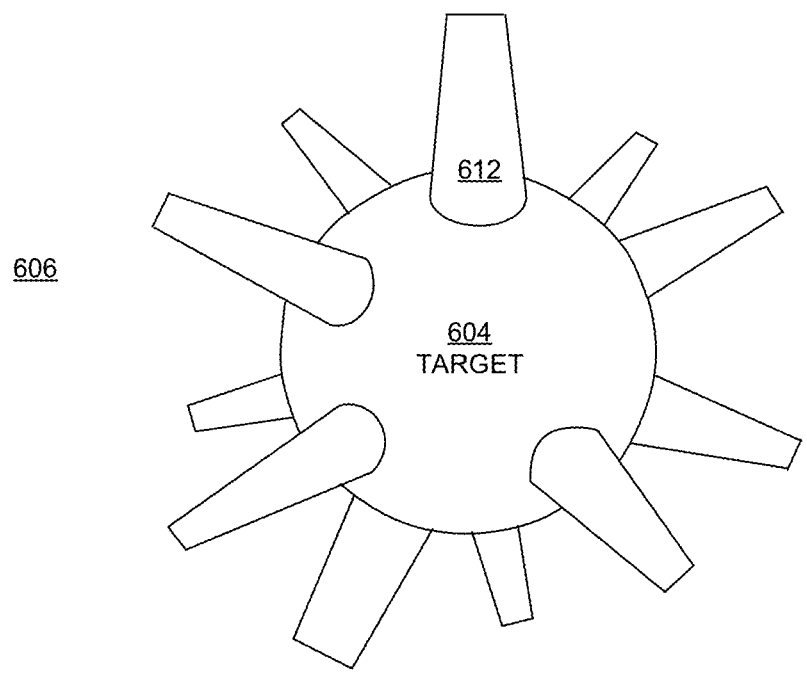
FIG. 6C illustrates a perspective view of an example of a beam geometry in embodiments according to the invention.

FIG. 6C illustrates a perspective view of an example of a beam geometry in embodiments according to the invention. In the example of FIG. 6C, the beams (exemplified by beam 612) are in different planes. As described herein, each beam can include one or more beam segments or beam lets. In this example, the beams' paths overlap only within the target 604, and do not overlap outside the target in the surrounding tissue 606. Although multiple beams are shown in the figure, all beams are not necessarily delivered at the same time or in overlapping time periods as mentioned above. Each beam can deliver a relatively high dose in a relatively short period of time. For example, each beam can deliver doses sufficient for FLASH RT.

For implementations that use proton beams or ion beams, the dose delivered by each beam at the respective proximal portion (or edge) of the target 604 may be different from (e.g., less than) the dose delivered by that beam at the respective distal portion (or edge) of the target (as before, proximal and distal are with reference to the source of the beam).

The dose delivered to each portion of the target 604 is cumulative, based on the number of beams that are delivered to and through that portion. Not all beams are depicted in the figures for simplicity; in general, the number of beams is sufficient to achieve a uniform cumulative dose distribution within the target 604.

In general, the surface of a target can be viewed as having a number of discrete facets. From this perspective, for beams other than photon beams, each incident beam is orthogonal to each facet such that the beams do not overlap outside the target. In the case of photon beams, each incident beam is parallel to the facet and does not overlap other beams outside the target.

Figure 7A:
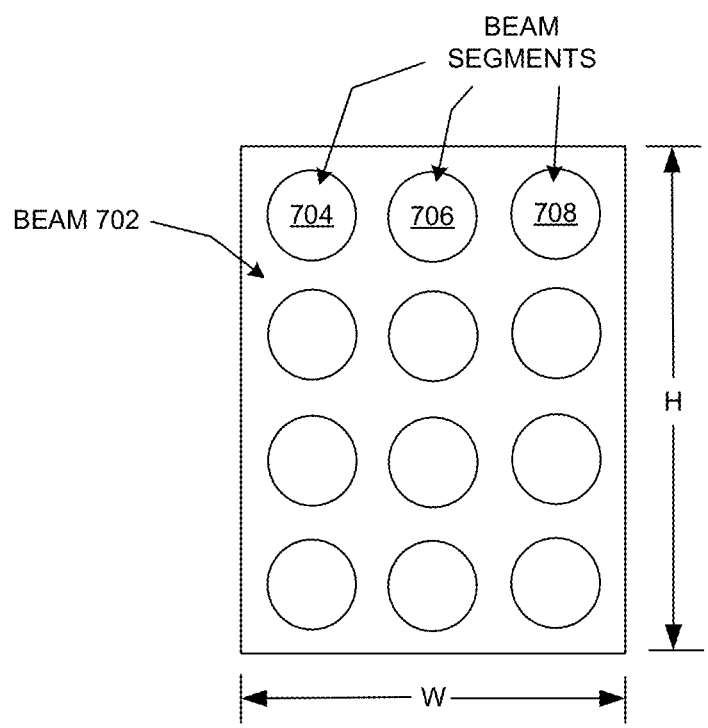
FIG. 7A illustrates a beam's eye view of a beam in embodiments according to the invention.

FIG. 7A illustrates a beam's eye view (BEV) of a beam 702 in embodiments according to the invention. That is, FIG. 7A illustrates a cross-section of a beam. The beams of FIGS. 6A, 6B, and 6C are examples of the beam 702. The beam 702 is illustrated as being rectangular in shape having a height H and width W. However, the invention is not so limited, and the beam 702 can have virtually any regular or irregular cross-sectional (e.g., BEV) shape. For example, the shape of the beam 702 can be defined using an MLC that blocks a portion or portions of the beam. Different beams can have different shapes.

In the FIG. 7A embodiment, the beam 702 includes a number of beam segments or beam lets (that also may be referred to as spots) exemplified by beam segments 704, 706, and 708. A maximum energy (e.g., 80 MeV) is specified for the beam 702, and an energy level is defined for each of the beam segments as a percentage or fraction of the maximum energy. By weighting the energy per beam segment, in effect the intensity of each beam segment is also weighted. The energy per beam segment is defined so that the beam segment will deliver a fraction of the prescribed dose such that, in combination with the other beam segments in the beam, and in combination with the other beams (and beam segments), a uniform (homogeneous) cumulative dose that satisfies the prescribed dose will be delivered within and across the volume of the target. The defined energy level or intensity can be realized for each beam segment using the beam energy adjuster 407 of FIG. 4A.

Each beam segment can deliver a relatively high dose in a relatively short period of time. For example, each beam segment can deliver at least 4 Gy in less than one second, and may deliver as much as 20 Gy or 50 Gy or more in less than one second. The energy or intensity of each beam segment can be controlled using the beam energy adjuster 407 of FIG. 4A so that the beam segment has sufficient energy to reach the distal edge of the target.

In operation, in embodiments, the beam segments are delivered sequentially. For example, the beam segment 704 is delivered to the target (turned on) and then turned off, then the beam segment 706 is turned on then off, then the beam segment 708 is turned on then off, and so on. Each beam segment may be turned on for only a fraction of a second (on the order of milliseconds).

Figure 7B:
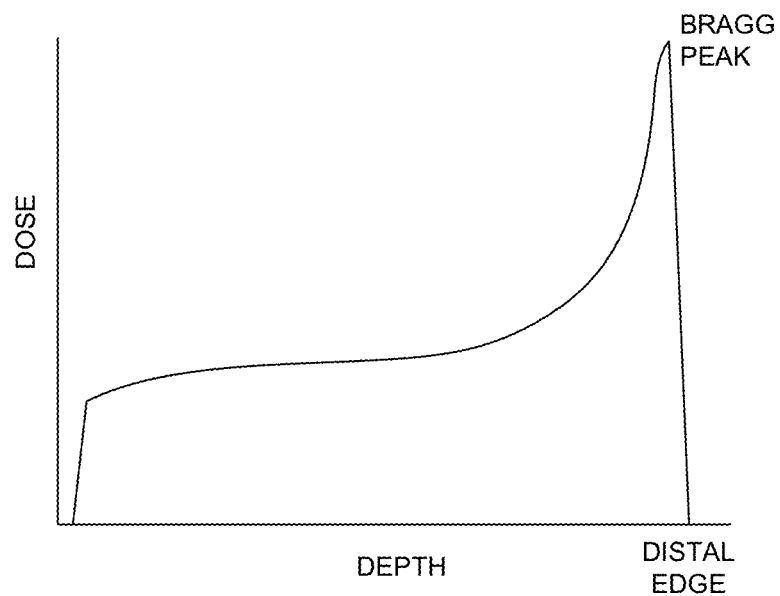
FIG. 7B is an example of a depth dose curve for a beam segment in embodiments according to the invention.

FIG. 7B is an example of a depth dose curve for a beam segment for a beam such as a proton beam or an ion beam that has a Bragg peak in embodiments according to the invention. The example of FIG. 7B shows calculated dose level as a function of depth in the target (distance from the beam source). The energy level or intensity of each beam segment can be controlled using the beam energy adjuster 407 (FIG. 4A) such that the Bragg peak is in the portion at (adjacent to or near) the distal edge of the target as shown in FIG. 7B.

With reference back to FIG. 6B, it can be seen (or deduced) that greater portions of each beam overlap toward the center of the target 604 than at the edges of the target, and more beams overlap at or near the center of the target 604 than at the edges of the target. For example, the beams 602 and 603 do not overlap at the proximal edge 608 of the target 604, overlap more toward the center of the target, overlap completely at or near the center of the target, and overlap partially past the center and at the distal edge 610. All beams overlap at the center of the target 604, but all beams do not overlap at the edges of the target. As mentioned previously herein, the dose contributed by each beam is cumulative, and the target 604 can be represented by the 3D elements known as voxels or sub-volumes. Each voxel or sub-volume will receive radiation from one or more beam segments delivered from different directions. The total dose for a voxel/sub-volume is the sum of the doses delivered by each beam segment received by the voxel. By shaping the beam segments as shown in the example of FIG. 7B for beams (e.g., proton beams and ion beams) that have a Bragg peak, the portions or voxels or sub-volumes in the target 604 that are traversed by fewer beams (beam segments) will receive a larger dose per beam segment because the Bragg peaks of those beam segments coincide with the locations of those portions/voxels/sub-volumes, while the portions/voxels/sub-volumes in the target that are traversed by more beams (beam segments) will receive a smaller dose per beam segment because the Bragg peaks of the latter beam segments do not coincide with the locations of the latter portions/voxels. In other words, the Bragg peak of each beam is at the distal edge of the target 604, where there is less overlap between beams, and the dose per beam is less than the Bragg peak at locations inside the target where there is more overlap between beams. In this manner, for embodiments that use beams that have Bragg peaks, a uniform dose can be delivered within and across the target 604.

FIG. 7C illustrates a cross-sectional view of an irregularly shaped target 715 and a beam 720 that includes four beam segments 721, 722, 723, and 724 in the longitudinal direction in embodiments according to the invention. As described above, the energy of each of the beam segments 721, 722, 723, and 724 can be individually defined and independently controlled (e.g., using the beam energy adjuster 407 of FIG. 4A) so that the beam segment has sufficient energy to reach the distal edge of the target 715. In particular, for beams like proton beams and ion beams that have Bragg peaks, the energy level of the beam segments 721, 722, 723, and 724 can be independently controlled using the beam energy adjuster 407 such that the Bragg peak of each beam segment is in the portion at (adjacent to or near) the distal edge of the target 715. In this manner, the range of the beam 720 can be shaped so that it follows the shape of the target 715 in the longitudinal direction. The cross-sectional size (e.g., height and width or diameter) of each beam segment can be specified according to the complexity of the shape of the target 715. For example, if the target surface is relatively uniform (e.g., flat), then the size of the beam segment can be larger.

FIG. 8 is a flowchart 800 of an example of a computer-implemented radiation treatment method in embodiments according to the present invention. The flowchart 800 can be implemented as computer-executable instructions residing on some form of computer-readable storage medium (e.g., using the control system 410 of FIG. 4).

In block 802 of FIG. 8, a radiation treatment plan is accessed. The radiation treatment plan includes a prescribed dose to be delivered uniformly across a target, a number of beams, directions of the beams, and beam energies for the beams, where the number of beams, the directions of the beams, and the beam energy for each of the beams are determined such that calculated cumulative doses at sub-volumes inside the target satisfy the prescribed dose. Such a radiation treatment plan can be generated using the methodology described in conjunction with FIG. 5.

In block 804, the beams are directed into the target according to the treatment plan, thereby delivering the prescribed dose uniformly across the target.

Figure 9:
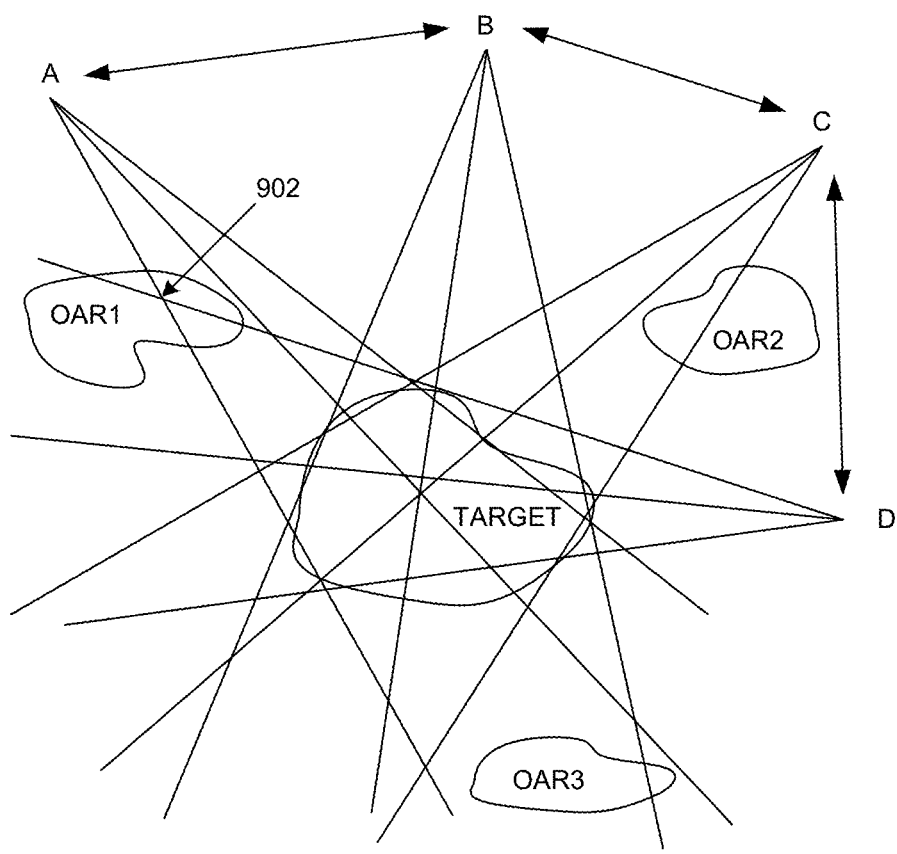
FIG. 9 illustrates a method of delivering radiotherapy treatments to in embodiments according to the invention.

FIG. 9 illustrates a method of delivering photon FLASH radiotherapy treatments to both a target (e.g., a tumor) and normal (healthy) tissue outside the target using a rapidly rotating (e.g., slip ring) gantry in embodiments according to the invention. In these embodiments, treatment is performed on a slice-by-slice or small volume-by-small volume basis using a type of IMRT such as volumetric modulated arc therapy (VMAT) or tomotherapy. In FIG. 9, three organs-at-risk (OAR1, OAR2, and OAR3) and a planning target volume (PTV; e.g., a tumor) are shown. As illustrated, OAR1 is irradiated twice at point 902 when the source is at two different gantry positions (A and D), thus leading to a finite Ti (the time between different irradiations to a single sub-volume). This implies that Ti is to be taken into consideration in treatment planning. The advantage of treating on a slice-by-slice basis is that MLC leaf speed requirements are reduced because MLC leaf travel lengths per unit time are reduced. In embodiments, to maintain the FLASH effect, movement of the gantry is controlled so it does not traverse more 180 degrees before advancing to the next slice in order to avoid opposing beams irradiating the same volume. Treatment may be delivered using modes such as continuous table motion or by step-and-shoot (SS). In both modes, care is taken to ensure that the transition regions between slices are still FLASH-type because some sub-volumes in the transition region could be (partly) irradiated from two different slice positions.

In the present embodiments, system requirements are illustrated by the following example. To deliver 20 Gy at a rate of 40 Gy/sec, the gantry should rotate though 180 degrees in less than 0.5 seconds (60 RPM). Assuming a five millimeter slice and an MLC modulation factor of three, required gantry and MLC leaf speeds on can be achieved using conventional radiotherapy devices. Technologies relevant to high speed MLCs include pneumatic or electromagnetic drives.

Figure 10A:
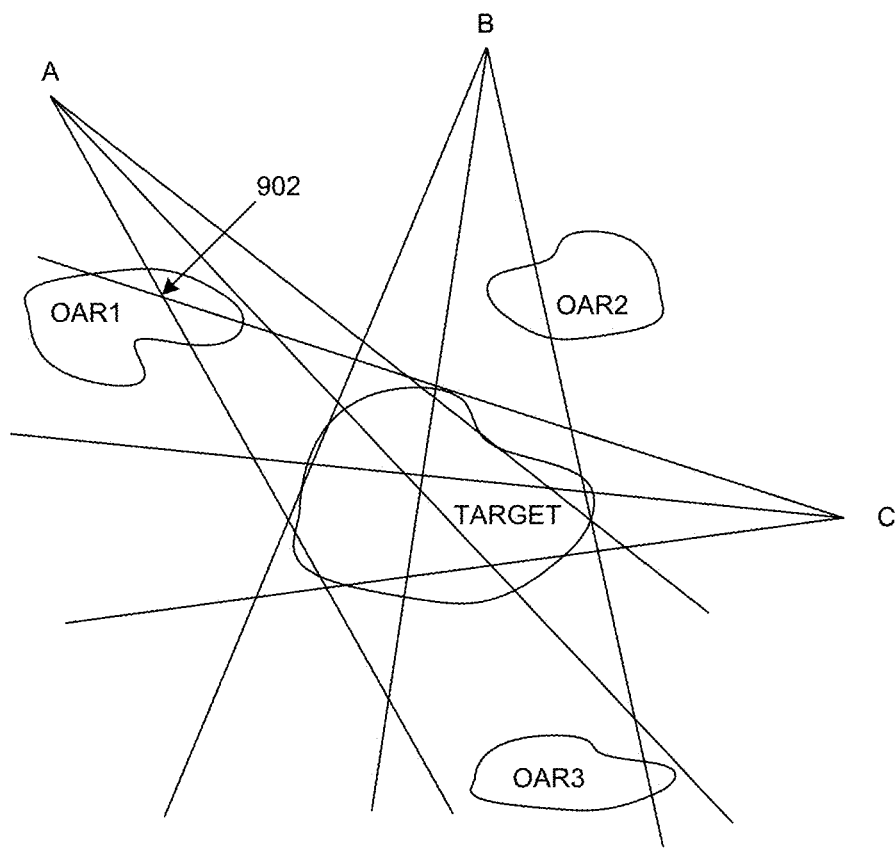
FIGS. 10A and 10B illustrate a method of delivering radiotherapy treatments in embodiments according to the invention.
Figure 10B:
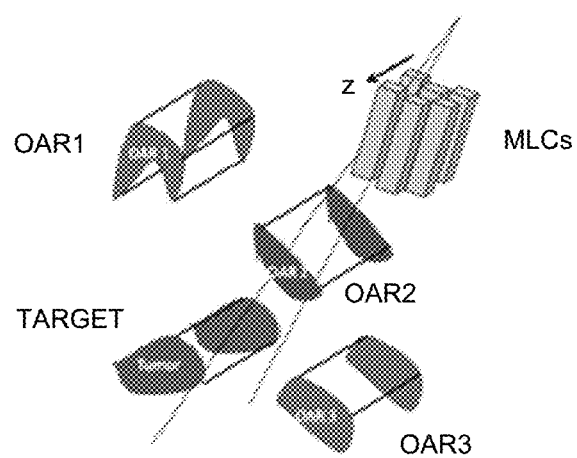

FIGS. 10A and 10B illustrate a method of delivering photon FLASH radiotherapy treatments using fixed gantry angles in embodiments according to the invention. In these embodiments, FLASH criteria are only maintained for normal tissue. In the FIG. 10 example, three fixed fields (A, B, and C) are shown in FIG. 10A. The MLC leaves can progress through the axial volume on a slice-by-slice base to minimize leaf travel distances and to minimize Ti. Treatment plans are accordingly devised so that a given volume of normal tissue is irradiated only through a minimal number of gantry angles to further minimize Ti. However, the PTV (e.g., tumor) may be irradiated from multiple gantry angles because, in some of the present embodiments, the FLASH criteria are not intended to be maintained.

Compared to the FIG. 9 embodiments, gantry rotation and MLC leaf speed requirements can be relaxed provided that the treatment plan is constrained so that a given volume of normal tissue is only irradiated from nearby gantry angles, thus minimizing Ti. In embodiments, the MLC should be able to move rapidly over a short distance equal to the slice thickness; this can be achieved using an MLC (e.g., a binary MLC) that employs pneumatic drives.

Figure 11:
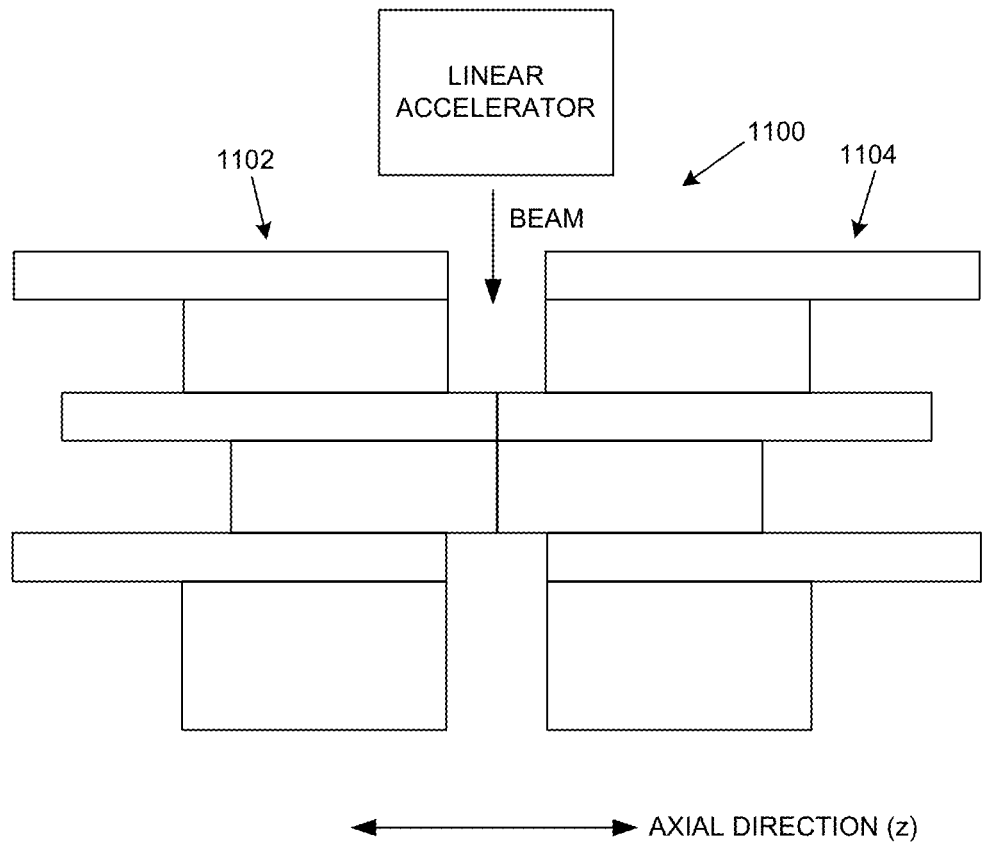
FIG. 11 illustrates a multileaf collimator in embodiments according to the invention.

FIG. 11 illustrates a quantized, multilayer MLC 1100 in embodiments according to the invention. In embodiments, each layer is only partially attenuating. In addition, in embodiments, the entire assembly is able to move in the axial (z) direction to cover multiple slices without having to move the patient. The motion in the axial direction need not be as fast as the rapid motion of the individual leaves. Also, it is not necessary to have both halves of the MLC assembly if leaf motion is sufficiently fast (e.g., either the leaves 1102 or the leaves 1104 can be replaced with a stationary or solid blocker).

In the embodiments of FIGS. 9, 10, and 11, delivered dose rates above 25 Gy/sec are achievable. In embodiments, Ti (the length of the time intervals separating different irradiations of the same sub-volume) can be advantageously reduced or minimized. For example, to deliver a total of four Gy in a single beam increment at a rate of 40 Gy/sec, the amount of time required is 0.1 seconds. In comparison, to maintain the dose rate criterion and deliver four Gy in two equal beam increments of two Gy each, each beam increment would be delivered in 0.05 seconds at a rate of 40 Gy/sec. It is desirable to reduce or minimize Ti (the time between the two increments) to satisfy the criterion of delivering a large dose in a short time and still be able to take advantage of the normal tissue sparing effect of FLASH RT. In effect, in this example, if the two beam increments pass through the same sub-volume of normal tissue, then that sub-volume may be considered to have been irradiated only once if Ti is short enough.

In summary, embodiments according to the invention improve radiation treatment planning and the treatment itself by expanding FLASH RT to a wider variety of treatment platforms and target sites. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified. Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to IMRT and IMPT, embodiments according to the invention can be used in spatially fractionated radiation therapy including high-dose spatially fractionated grid radiation therapy and microbeam radiation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computing system comprising:
   a central processing unit (CPU); and
   memory coupled to the CPU and having stored therein instructions that, when executed by the computing system, cause the computing system to execute operations to generate a radiation treatment plan, the operations comprising:
   accessing a minimum prescribed dose to be delivered into and across a target;
   determining a number of beams and directions of the beams, wherein the directions are determined such that the beams do not overlap outside the target, and wherein each beam of the beams comprises a plurality of beam segments;
   determining a maximum beam energy for said each beam; and
   for said each beam, determining a beam segment energy for each beam segment of the plurality of beam segments as a percentage of the maximum beam energy, wherein the number of the beams, the directions of the beams, and the maximum beam energy for said each beam are determined such that the entire target receives the minimum prescribed dose.

2. The computing system of claim 1, wherein the beams overlap inside the target.

3. The computing system of claim 1, wherein the beams comprise beams having paths that are in a same plane.

4. The computing system of claim 1, wherein the beams comprise beams having paths that are in different planes.

5. The computing system of claim 1, wherein the beams are selected from the group consisting of proton beams and ion beams and have a respective Bragg peak associated therewith, wherein saki each beam segment is controlled to position its respective Bragg peak in a portion of the target at a distal edge of the target.

6. The computing system of claim 1, wherein the number of the beams, the directions of the beams, and the maximum beam energy for said each beam are determined using an iterative process, wherein the operations further comprise adjusting the number of the beams, the directions of the beams, and the maximum beam energy for said each beam in the iterative process.

7. A non-transitory computer-readable storage medium having computer-executable instructions for causing a computing system to perform a method of radiation treatment planning, the method comprising:
   accessing information specifying a prescribed dose to be delivered into and throughout a target;
   determining a number of beams to be directed into the target;
   determining gantry angles for directing the beams into the target; and
   determining a beam energy for each of the beams, wherein the number of beams, the gantry angles, and the beam energy for each of the beams are determined such that the beams do not overlap outside the target and calculated cumulative doses at all sub-volumes inside the target satisfy the prescribed dose; wherein said each of the beams comprises a respective plurality of beam segments, wherein the method further comprises:
   determining a respective maximum beam energy for said each of the beams; and
   determining a beam energy for each beam segment of each of the respective plurality of beam segments as a percentage of the respective maximum beam energy.

8. The non-transitory computer-readable storage medium of claim 7, wherein the gantry angles are determined such that the beams overlap inside the target.

9. The non-transitory computer-readable storage medium of claim 7, wherein the gantry angles are determined such that the beams are in a same plane.

10. The non-transitory computer-readable storage medium of claim 7, wherein the gantry angles are determined such that the beams are in different planes.

11. The non-transitory computer-readable storage medium of claim 7, wherein the beams are selected from the group consisting of proton beams and ion beams and have a respective Bragg peak associated therewith, wherein said each beam segment of said each of the respective plurality of beam segments is controlled to position its respective Bragg peak in a portion of the target at a distal edge of the target.

12. A radiation treatment method, comprising:
    accessing a prescribed dose to be delivered uniformly across a target;
    determining a number of beams and directions of the beams, wherein the directions are determined such that the beams do not overlap outside the target, and wherein each beam of the beams comprises a plurality of beam segments;
    determining a maximum beam energy for said each beam;
    determining a beam segment energy for each beam segment of the plurality of beam segments as a percentage of the maximum beam energy, wherein the number of the beams, the directions of the beams, and the maximum beam energy for said each beam are determined such that the entire target receives the prescribed dose, and wherein the number of the beams, the directions of the beams, the maximum beam energy for said each beam, and the beam segment energy for said each beam segment comprise elements of a radiation treatment plan; and
    directing the beams into the target according to the radiation treatment plan.

13. The method of claim 12, wherein the beams overlap inside the target.

14. The method of claim 12, wherein paths of the beams are in a same plane.

15. The method of claim 12, wherein paths of the beams are in different planes.

16. The method of claim 12, wherein the beams are selected from the group consisting of proton beams and ion beams and have a respective Bragg peak associated therewith, wherein each beam segment is controlled to position its respective Bragg peak in a portion of the target at a distal edge of the target.

* * * * *